(12) United States Patent
Yukawa et al.

(10) Patent No.: US 7,816,109 B2
(45) Date of Patent: Oct. 19, 2010

(54) MICROORGANISM HAVING THE IMPROVED GENE FOR HYDROGEN-GENERATING CAPABILITY, AND PROCESS FOR PRODUCING HYDROGEN USING THE SAME

(75) Inventors: Hideaki Yukawa, Kyoto (JP); Masayuki Inui, Kyoto (JP); Akihito Yoshida, Nari (JP); Naoto Torata, Kashihara (JP)

(73) Assignees: Research Institute of Innovative Technology for the Earth, Kyoto (JP); Sharp Corporation, Osaka (JP)

( * ) Notice: Subject to any disclaimer, the term of this patent is extended or adjusted under 35 U.S.C. 154(b) by 719 days.

(21) Appl. No.: 11/653,432

(22) Filed: Jan. 16, 2007

(65) Prior Publication Data

US 2007/0202585 A1    Aug. 30, 2007

(30) Foreign Application Priority Data

Jan. 13, 2006 (JP) ............................. 2006-005645
Dec. 27, 2006 (JP) ............................. 2006-351924

(51) Int. Cl.
*C12P 3/00* (2006.01)
*C12P 1/04* (2006.01)
*C12N 1/21* (2006.01)
*C12N 9/02* (2006.01)
*C07K 14/00* (2006.01)
*C07H 21/00* (2006.01)

(52) U.S. Cl. ...................... 435/168; 435/170; 435/189; 435/252.33; 530/350; 536/23.2

(58) Field of Classification Search .............. 435/252.3, 435/252.33, 189, 170, 168; 530/350; 536/23.2
See application file for complete search history.

(56) References Cited

U.S. PATENT DOCUMENTS 7,432,091 B2   10/2008   Yukawa et al.

FOREIGN PATENT DOCUMENTS

WO   WO 2004/074495 A1   9/2004

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Zhou et al., Cell Mol Life Sci 63(19-20):2260-2290.*
Kozak, M., Gene 234:187-208, 1999.*
Yoshida et al., Applied Microbiology and Biotechnology 73:67-72, available online May 9, 2006.*
Sode et al., Applied Biochemistry and Biotechnology 77-79:317-323, 1999.*
Yoshida et al., Applied and Environmental Microbiology 71(11):6762-6768, 2005.*
Alam et al., *Anaerobic Fermentation Balance of Escherichia coli as Observed by In Vivo Nuclear Magnetic Resonance Spectroscopy*, Journal of Bacteriology, Nov. 1989, vol. 171, No. 11, pp. 6213-6217.
Kumar et al., *Redirection of biochemical pathways for the enhancement of $H_2$ production by Enterobacter cloacae*, Biotechnology Letters, 23: 537-541, 2001.
Sode et al, "Metabolic Engineering Approaches for the Improvement of Bacterial Hydrogen production Based on *Escherichia coli* Mixed Acid Fermentation", Biohydrogen II, May 1, 2001, pp. 195-204.

* cited by examiner

*Primary Examiner*—Delia M Ramirez
(74) *Attorney, Agent, or Firm*—Nixon & Vanderhye P.C.

(57) ABSTRACT

A hydrogen producing method by culturing a microorganism having a hydrogenase gene, in which a lactic acid biogenetic path and a succinic acid biogenetic path in anaerobic metabolic paths are inactivated, under an anaerobic condition in the presence of organic substrate. The microorganism may further have a formate dehydrogenase gene. The microorganism may be *Escherichia coli* which is a facultative anaerobic bacterium.

5 Claims, 2 Drawing Sheets

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
cctgtttcgc ttcaccggtc ag       22

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tctttggttc tgtccagtac cg       22

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
ggactagtct ggcgttcgat ccgtatcc       28

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gctctagacc aaaacctttc agaatgcgca       30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gctctagaac ggaagatcac ttcgcagaat       30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
ggactagttt aagggcacca ataactgcct       30

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ctctgcatgc aacccatcac atatacctgc       30

<210> SEQ ID NO 8
<211> LENGTH: 30
<212> TYPE: DNA
<213> ORGANISM: Artificial Sequence
<220> FEATURE:

<223> OTHER INFORMATION: Primer

<400> SEQUENCE: 8
ctctgcatgc atcgatcctc tagagtatcg          30

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
gcgagctcgt gcaaaccttt caagccga          28

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
cgggatccga caccaatcag cgtgacaa          28

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ccgctcgagc tgaacccaga gttcatcgg          29

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
ccgctcgaga acgtacgctt tcgccagtt          29

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
ccgctcgagg aagatgcgtg atctgatcct          30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
ccgctcgagg ccacgttgtg tctcaaaatc          30

MICROORGANISM HAVING THE IMPROVED GENE FOR HYDROGEN-GENERATING CAPABILITY, AND PROCESS FOR PRODUCING HYDROGEN USING THE SAME

BACKGROUND OF THE INVENTION

1. Field of the Invention

The present invention relates to a process for producing hydrogen with use of a microorganism possessing the hydrogenase gene and having the lactic acid and succinic acid biogenetic pathways inactivated in its anaerobic metabolic pathways. The hydrogen generated by the process of the present invention is usable as a fuel for fuel cells.

2. Description of the Related Art

Hydrogen has an increased attention as an ultimate clean energy source, which, unlike fossil fuels, does not liberate any environmentally controversial substances through combustion, such as carbon dioxide gas, sulfur oxide and the like. Hydrogen can deliver a heat quantity per unit mass three times or more greater than petroleum oils, and when supplied to fuel cells, can be converted into electric and thermal energies with a high degree of efficiency.

As a conventional chemical process for production of hydrogen, for example, there have been proposed several technologies, inclusive of the thermal-cracking or steam reforming process of natural gas or naphtha. These production technologies need the reactions conditions of high temperature and high pressure, while they yield the synthesis gas containing CO (carbon monoxide), and such gas, on the occasion of utilization in fuel cells, is consequently required to be freed of CO to circumvent the problem of poisoning of fuel-cell electrode catalysts. However, the removal of CO is technically-difficult and cannot be said to be easy.

On the other hand, the method of biological hydrogen generation by microorganisms can be conducted into practice under the reaction conditions of ambient temperature and atmospheric pressure, and the generated gas does not need the removal of CO, because it does not contain CO.

From described standpoints, the method of biological hydrogen generation with use of microorganisms is attracting enhanced attention as a more preferred means of supplying a fuel intended for use in fuel cells.

The method of biological hydrogen generation is roughly classified into the two methods: method using a photosynthetic microorganism and the method with use of a non-photosynthetic microorganism (mainly an anaerobic microorganism).

The former method, although it uses the energy of light for generation of hydrogen, needs a vast light capturing surface area because of its low utilization efficiency of the energy of light, and encounters many unsolved problems, such as the expensive cost investment for the hydrogen production facilities and difficulties in securing its maintenance administration, thus having still been considered not to reach the stage of commercialization.

With reference to the latter method, there have been known the various metabolic pathways being responsible for generating hydrogen by the anaerobic microorganisms. Such metabolic pathways include, for example, the pathway of generating hydrogen during the step of decomposition of glucose to pyruvic acid; the pathway of generating hydrogen during the step of production of acetic acid from pyruvic acid via acetyl CoA; or the pathway of generating hydrogen directly from formic acid originating from pyruvic acid, and the like. The hydrogen generation, which is conjugated with reoxidation of NADH and the like in the step of decomposition of glucose to pyruvic acid or in the step of production of acetic acid from pyruvic acid via acetyl CoA, is frequently found to take place in obligetory anaerobic microorganisms. The pathway of generating hydrogen directly from formic acid originating from pyruvic acid is working, as a formic acid hydrogen lyase system (hereinafter, referred to briefly as "FHL system"), in lots of different microorganisms including facultative anaerobic microorganisms, and the FHL system has been investigated extensively in the species *Escherichia coli*. The generation of hydrogen from glucose by facultative anaerobic bacteria, which may be typified by *Escherichia coli*, is considered to proceed through the successive steps of producing two molecules of pyruvic acid generated from one molecule of glucose and producing two molecules each of acetyl CoA and formic acid from one mole of glucose through cleavage of pyruvic acid into acetyl CoA and formic acid, followed by decomposition of formic acid to hydrogen and carbon dioxide. Accordingly, the theoretical yield of the hydrogen generation from one molecule of glucose by such facultative anaerobic bacteria is regarded as 2 molecules.

There have been known so far several processes for producing hydrogen from glucose used as a substrate through the FHL system, and a research paper was published on the process for producing hydrogen by the method of inactivation of the lactic acid biogenetic pathway in *Escherichia coli*.

Koji Sode et al. in Biohydrogen II, 2001, p. 195-204 disclosed the process for producing hydrogen from glucose using the microorganism having its lactic acid generation pathway inactivated. However, it is noticed that the hydrogen yield was hardly improved in spite of the fact that the lactic acid generation pathway was inactivated, as may be reflected by the description mentioning that the hydrogen yield from glucose was realized merely in the range of as low as about 22% to 24% to the theoretical yield, while at the same time, the rate of hydrogen generation was not improved, as well.

The Official Gazette of WO 2004/074495 discloses the method for providing a microorganism capable of generating hydrogen, which method comprises culturing a microorganism under aerobic conditions and culturing the resultant microbial cells under anaerobic conditions to impart the hydrogen generating capability to the microorganism. However, the publication does not make mention of improvements both in rate of hydrogen generation and hydrogen yield to be attained through gene modification.

K. Y. ALAM et al., in J. Bacteriol., 1989, Vol. 171, p. 6213-6217, reported the generation balance of organic acids and the like in relation to various substrates having different levels of oxidation-reduction potential. This literature reference describes that there was obtained the microorganism capable of suppressing the generation of lactic acid and succinic acid through inactivation of the lactate dehydrogenase gene (hereinafter also referred to briefly as ldhA) and also the fumarate reductase gene (hereinafter also referred to as frdABCD), whereas it does in no way describe anything about the hydrogen generation and hydrogen yield, although it gives the description about the oxidation-reduction potential balance of the resultant products. The fumarate reductase is considered to be composed of four subunits of four kinds of the proteins encoded by the four genes, frdA, frdB, frdC, and frdD, to elicit the enzymatic activity as a composite enzyme, whereas the said literature reference does neither describe how the fumarate reductase (FRD) was inactivated nor indicate which subunit was inactivated.

The said literature reference, in Table 3 (page 6215), presents the compositions of various organic acids and the like generated from different types of saccharides used, and also describes the data demonstrating that the mutant strains, which had the lactate dehydrogenase gene and fumarate reductase gene frd inactivated, exhibited almost no change in the generation amount of formic acid supposedly associated with the hydrogen generation, as compared with the wild-type. The document does neither suggest the procedural technique of improving the yield and rate of hydrogen generation from saccharides nor infer the relevant phenomena with increasing hydrogen production.

Biotechnol Lett., 2001, 23, p537-541, discloses that the hydrogen yield was greatly increased by inactivating the anaerobic metabolism pathway with use of a mutagenic substance. However, the report does neither specify the inactivated gene nor describe anything about succinic acid.

The official Gazette of PCT/JP2004/002092 discloses a process for producing hydrogen with a highly enhanced efficiency, but the method poses restriction on the conditions for culturing microbial cells in the presence of formic acid, and does not teach any improvement of the hydrogen yield to be attained by the microorganism through genetic recombination.

With reference to the hydrogen yield from an organic substrate under anaerobic conditions, for example, the theoretical hydrogen yield is 2 molecules per molecule of glucose. In practice, however, it is difficult to generate hydrogen in the theoretical yield, because discharge of the reductive power which is the basic working principle of energy source for the hydrogen generation by anaerobic microorganisms, is used in other forms different from the hydrogen generation. In addition, the methods for producing hydrogen with use of a microorganism suffer from the disadvantage that the rate of hydrogen generation is slow.

SUMMARY OF THE INVENTION

It is the first object of the present invention to provide a process for producing hydrogen from an organic substrate with use of a microorganism in improved yields and at accelerated rates, wherein the thus obtained hydrogen may be usable as a fuel for fuel cells.

It is the second object of the present invention to provide a microorganism capable of producing hydrogen from an organic substrate in improved yields and at accelerated rates.

With a specific view to solving the above-described problems, the present inventors conducted intensive investigation, and as a result, found that the reaction of hydrogen generation from an organic substrate can be carried out under anaerobic conditions with use of the microorganism possessing the hydrogenase gene and having the lactic acid and succinic acid biogenetic pathways inactivated in its anaerobic metabolic pathway, resulting in not only marked improvement in hydrogen yield from the organic substance but also significant increases in rate of hydrogen generation per unit weight of the microorganism. On the basis of such finding, the present inventors performed further investigation, leading to completion of the present invention.

Namely, the present invention provides a process for producing hydrogen and a microorganism, both of which are to be described below.

Item 1. A process for producing hydrogen which comprises culturing a microorganism, which possesses the hydrogenase gene and has the lactic acid and succinic acid biogenetic pathways inactivated in its anaerobic metabolic pathway, in the presence of an organic substrate under anaerobic conditions;

Item 2. The process for producing hydrogen as described above under Item 1, wherein the microorganism further possesses the formate dehydrogenase gene;

Item 3. The process for producing hydrogen as described above under Item 1, wherein the microorganism is a facultative anaerobic bacterium;

Item 4. The process for producing hydrogen as described above under Item 3, wherein the facultative anaerobic bacterium is a transformant of *Escherichia coli*;

Item 5. The process for producing hydrogen as described above under Item 1, wherein the microorganism possesses the inactivated lactate dehydrogenase and the inactivated at least one of the genes encoding the subunits which make up of the fumarate reductase.

6. The process for producing hydrogen as described above under Item 1, wherein the microorganism is the W3110 ΔldhA ΔfrdBC strain of *Escherichia coli* (deposited with International Patent Organism Depositary Authority, National Institute of Advanced Industrial Science and Technology of Japan, under the accession No. FERM P-20737, and under the international accession No. FERM BP-10726);

7. The process for producing hydrogen as described above under Item 1, which comprises further effecting culture under anaerobic conditions after culturing the microorganism under aerobic conditions;

8. The process for producing hydrogen as described above under Item 1, wherein the organic substrate is saccharides;

9. The process for producing hydrogen as described above under Item 1, wherein the saccharides are at least one kind selected from the group consisting of glucose, galactose, xylose, sucrose and fructose; and 10. The W3110 ΔldhA ΔfrdBC strain of *Escherichia coli* (deposited with International Patent Organism Depositary Authority, National Institute of Advanced Industrial Science and Technology of Japan, under the accession No. FERM P-20737 and under the international accession No. FERM BP-10726).

According to the present invention, the efficient hydrogen generation from an organic substrate, such as saccharides, etc., is feasible. Furthermore, it is attainable to increase the rate of hydrogen generation per weight of the microorganism from an organic substrate and also to reduce the volume capacity of the hydrogen generation reactor. Also, it becomes achievable to suppress the generation of by-products, such as organic acids and the like, during hydrogen generation.

DETAILED OF THE INVENTION

Figure 1:
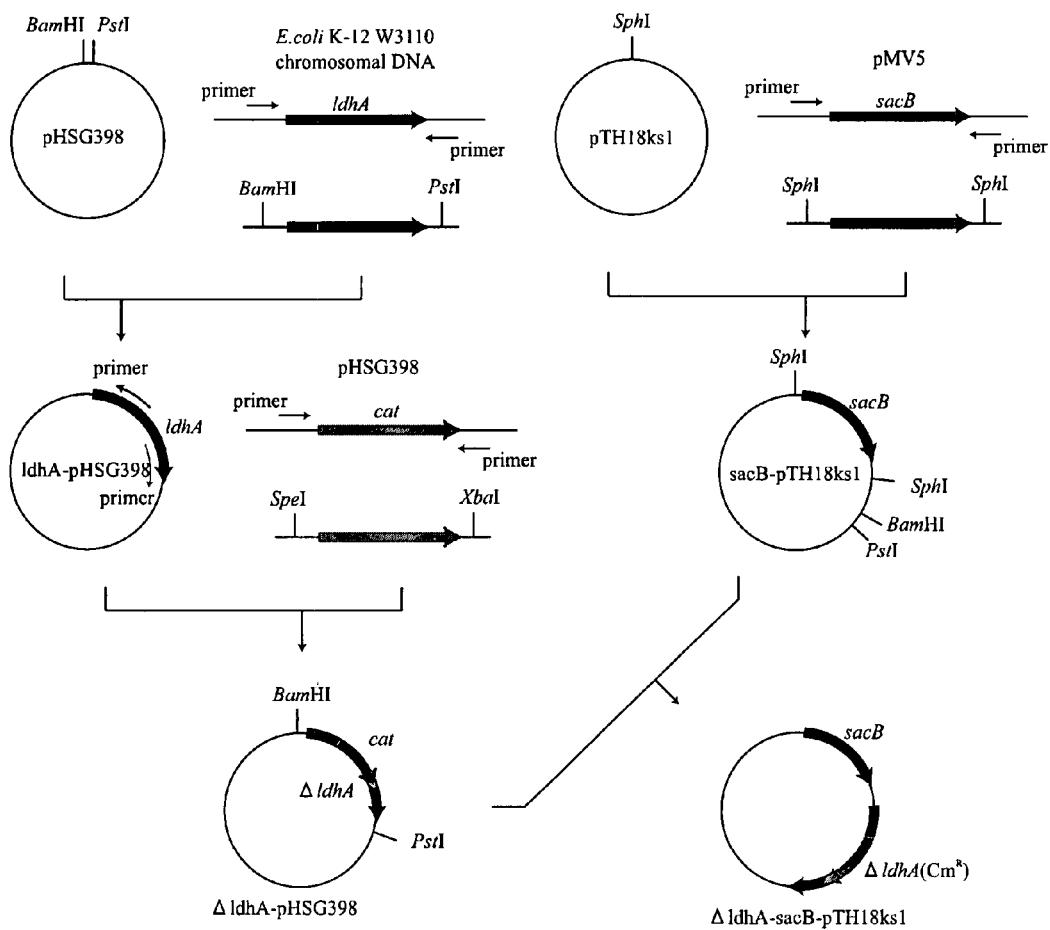
FIG. 1 is a schematic view showing the construction of ΔldhA-sacB-pTH18ks1.

The process for producing hydrogen according to the present invention is realized by using a microorganism possessing the hydrogenase gene and having the lactic acid and succinic acid biogenetic pathways inactivated in its anaerobic metabolic pathway. Such microorganism is suspended in a liquid for the hydrogen generation, and the suspension is supplied with an organic substrate under anaerobic conditions to thereby enable the industrially advantageous generation of hydrogen to be performed. To be described below in detail is the present invention.

The microorganisms to be used for construction of the microorganism of the present invention are selected from the microorganisms possessing the hydrogenase gene. Typical examples of the hydrogenase include the hydrogenase contained in the formate hydrogen lyase complex (R. Boehm et al., Molecular Microbiology, 1990, Vol. 4, p. 231-243) and the soluble hydrogenase existing as a monomer within the cell (J. Mishra et al., Biochemical and Biophysical Research Communications, 2004, Vol. 324, pp. 679-685). Such hydrogenase catalyzes the conversion to one molecule of hydrogen from two protons and electrons. As the hydrogenase, there may be mentioned, for example, the hydrogenases using formic acid, NAD(P)H, ferredoxin, cytochrome or menaquinone and the like as a substrate.

It is preferable that such microorganism further possesses the formate dehydrogenase gene (F. Zioni et al., Proc. Natl. Acad. Sci. USA, 1986, Vol. 83, p. 4630-4654). The formate dehydrogenase gene is contained in the formate hydrogen lyase complex.

The hydrogenase activity to be exhibited by a microorganism can be identified and determined by extracting a crude enzyme liquid from microbial cells, and carrying out the reaction of reducing $NAD^+$, benzyl viologen or methyl viologen and the like on the basis of the enzymatic reaction using hydrogen as a substrate, followed by detection of any changes in absorbance. On the other hand, the formate dehydrogenase gene to be possessed by a microorganism can be identified and established by extracting a crude enzyme liquid from microbial cells, adding sodium formate to the crude enzyme liquid to carry out the reaction of reducing benzyl viologen and the like, followed by detection of any changes in absorbance. Such enzymes to be possessed by a microorganism may be identified and determined by conducting Western blotting with a protein prepared from the microorganism using the hydrogenase antibody prepared in mice or rats. Alternatively, such enzymes may be identified by conducting Southern hybridization to a DNA sequence extracted from the microorganism using a probe designed on the basis of the base sequence conserved between different hydrogenases or between different formate dehydrogenases.

Preferably, the microorganism to be used in the construction of the microorganism being usable in the present invention is anaerobic microorganisms. The anaerobic microorganism may be exemplified by obligate anaerobic microorganisms or facultative anaerobic microorganisms, but facultative anaerobic microorganism is more preferable than obligate anaerobic microorganism. Examples of the facultative anaerobic microorganism include microorganisms of the genus *Escherichia*, such as *Escherichia coli* ATCC9637, ATCC11775, ATCC4157, ATCC27325, etc., microorganisms of the genus *Klebsiella*, such as *Klebsiella pneumoniae* ATCC13883, ATCC8044 etc. or microorganisms of the genus *Enterobacter*, such as *Enterobacter aerogenes* ATCC13048, ATCC29007 etc. or *Enterobacter cloacae*, while examples of the obligatery anaerobic microorganism include microorganisms of the genus *Clostridium*, such as *Clostridium beijerinckii* ATCC25752, ATCC17795 etc., *Clostridium butylicum* or *Clostridium acetobutylicum*.

These anaerobic microorganisms are preferably cultured under aerobic conditions, because the microbial division and proliferation proceeds much slower under anaerobic conditions than under aerobic conditions. Among anaerobic microorganisms, in this context, facultative anaerobic microorganisms can be more suitably used than obligatery anaerobic microorganisms in the process for producing hydrogen according to the present invention. Among the above microorganisms, *Escherichia coli, Enterobacter aerogenes* and the like are appropriately used in the process for producing hydrogen according to the present invention.

In the microorganism to be used in the method of the present invention, the lactic acid and succinic acid biogenetic pathways in the anaerobic metabolic pathway are allowed to undergo inactivation. In the present invention, the term "inactivation" is understood to comprehend both the case where the microorganism does not substantially exhibits the activity and the case where the microorganism shows decreased activity as compared with the native counterpart.

As a procedure of inactivating the lactic acid and succinic acid biogenetic pathways, for example, the procedure of genetic recombination of the microorganism so as to allow the lactic acid and succinic acid biogenetic generation to be ultimately suppressed in its anaerobic metabolic pathway. The more specific examples of such procedure include the non-genetic engineering technique based on mutagenesis using a mutagen, and the genetic engineering technique involving manipulation of the desired gene sequence with use of restriction enzymes, ligases and the like. In these techniques, the genetic engineering technique is more preferred in order to secure the inactivation of the targeted genes.

In order to inactivate the lactic acid biogenetic pathway in the anaerobic metabolic pathway owned by the microorganism according to the present invention to thereby suppress the lactic acid generation, it is preferable to inactivate the genes involved in the lactic acid biogenetic pathway, for example, the lactate dehydrogenase gene. In the succinic acid biogenetic pathway, phosphoenol pyruvic acid is converted to succinic acid via oxaloacetic acid, malic acid and fumaric acid. In the microorganism of the present invention, any step of the succinic acid biogenetic pathway in the anaerobic metabolic pathway may be inactivated, but the step of generating succinic acid from fumaric acid is preferably inactivated. For the purpose of this, it is preferred to inactivate the gene involved in the succinic acid biogenetic pathway, for example, the fumarate reductase gene.

With reference to the fumarate reductase gene, at least one of the genes that encode subunits of the fumarate reductase may be inactivated.

As the procedure of inactivating the lactate dehydrogenase and fumarate reductase genes through the genetic engineering technique, preferred use is made of the procedure which involves cloning in advance the lactate dehydrogenase and fumarate reductase genes, then causing mutation at the specifically determined site of the said gene through a non-genetic engineering or genetic engineering technique, providing a deletion site of the specifically determined length at the specifically determined site of the gene by a genetic engineering technique or introducing an exogenous gene, such as a drug (antibiotic drugs, such as kanamycin or hygromycin) resistant marker, to the specifically determined site of the gene, and the like, to thereby provide for a DNA sequence containing the mutant gene for inactivation, followed by returning the DNA into cells.

When the lactate dehydrogenase and fumarate reductase genes are inactivated by introducing a drug resistant marker therein, screening can be effected for the targeted strain on a culture medium containing the drug resistance marker to give the strain having the drug resistant marker introduced. This procedure in some instances allows exogenous genes, such as a gene for a drug resistant marker, to exert influences on the neighboring or peripheral genes. As the procedure of permitting such situations to be avoided, it is desirable to provide the lactate dehydrogenase and fumarate reductase genes with a deletion site of the specifically determined length. Since mere deletion of a DNA sequence of the specifically determined length cannot allow the inactivated strains to be produced, it may be possible to provide the gene with a deletion site of the specifically determined length by concurrently introducing the gene to be inactivated and a lethal gene into a cell, followed by homologous recombination. The lethal gene includes, for example, the sacB gene from *Bacillus subtilis* in case when the above two genes are introduced in a cell of *Escherichia coli*. A gene having a deletion site of the specifically determined length and the sacB gene are inserted into a vector for transformation, and this vector is introduced to a host to be subjected to homologous recombination, followed by homologous recombination. In order to effect homologous recombination efficiently, it is more preferable to use a temperature-sensitive vector. The temperature-sensitive vector may be exemplified by pMA2, pLOI2226, pTH18ks1, pTH18ks5 and the like, all of which have the temperature-sensitive replicon pSC101ts. The host, after being once subjected to homologous recombination, has both the inactivated gene and the natively existing, non-inactivated gene in coexistence within itself. By culturing the host cell after being once subjected to homologous recombination under such conditions as may induce the lethal gene, the second homologous recombination is allowed to take place between the lethal gene region and the non-inactivated gene region to thereby inactivate the lactate dehydrogenase gene or the fumarate reductase gene completely, thus enabling the targeted recombinant strain to be obtained.

Insertion into a vector (plasmid) of the gene to undergo recombination may be achieved by the procedures known in the art, and it is simple and practical and therefore preferable to use the commercially available ligation kits and the like. The ligation kit may be exemplified by DNA ligation Kit ver 1, DNA ligation Kit ver 2.1 (produced by TAKARA BIO INC.), Fast-Link (trade mark); DNA Ligation Kit(produced by AR BROWN CO., LTD), Ligation-Convenience Kit (produced by NIPPON GENE CO., LTD.) or rapid DNA ligation kit (produced by Roche Diagnostics) and the like.

The procedure of introducing the vector obtained in the above-described manner into a host can be practiced with use of the known procedures. The said known procedure includes, for example, the procedure of treating the competent cells with calcium chloride (Mandel, M. and Higa, A., J. Mol., Biol., 53, 159(1970)), the procedure of introducing the cells after being rendered into the form of protoplast or spheroplast (Chang, S. and Choen, S. N., Molec. Gen., Genet., 168.111(1979); Bibb, M. J., Ward, J. M. and Hopwood, O. A., Nature, 274, 398(1978); Hinnen, A., Hicks, J. B. and Fink, G. R., Proc. Natl. Acad. Sci. USA, 75 1929(1978)), the procedure of electroporation (Canadian Journal of Microbiology, 43197 (1997)) and the like.

The gene involving lactic acid and succinic acid biogenetic pathways inactivated may be obtained by identifying the lactate dehydrogenase and fumarate reductase genes, etc. through the literature survey or by the known molecular biological experiments or homology search derived therefrom, etc., and selecting the gene with use of the identified sequence, followed by recombination with use of the above-mentioned operational procedures. In more detail, the *Escherichia coli* K-12 W3110 strain has been decoded for the DNA sequences of the full genome, and the DNA sequences of the lactate dehydrogenase gene ldhA and the fumarate reductase gene frdABCD existing in the said strain W3110 can be found out by searching the databases described in the following URLs:

DDBJ DNA Data Bank of Japan Genome Information Broker

Genome Analysis Project in Japan—Escherichia coli K-12 W3110

On the basis of the DNA sequences thus obtained, the DNA sequences containing the ldhA gene and the frdABCD gene can be amplified, and the genes obtained in this manner may be inactivated by recombination through the above-mentioned operational procedures. On the occasion of this, the lactate dehydrogenase is the single enzyme encoded by the gene ldhA, and the fumarate reductase is the enzyme encoded by the gene frdABCD and made up of the four subunits.

Alternatively, the sequences which are highly homologous with ldhA and frdABCD, respectively, may be searched through the database described in the following URL, and the relevant genes can be screened using the sequences:

DDJB DNA Data Bank of Japan Blast Version 2.2.18

Inactivation of the lactate dehydrogenase and fumarate reductase genes according to the present invention may be conducted with use of any of the above-mentioned procedures.

In this manner, it is possible to create the microorganism having the lactic acid and succinic acid biogenetic pathways inactivated.

To be illustrated below are the culturing method to enable the microorganism created by the above-described procedure to acquire the hydrogen-generation capability, and the process for producing hydrogen with use of such microorganism.

The process for producing hydrogen according to the present invention includes, for example, the process for allowing the hydrogen generation concurrently with anaerobic proliferation of the microorganism and the process for carrying out the hydrogen generation as divided into the step of culturing the microorganism and the step of generating hydrogen under anaerobic conditions. Preferred from the standpoint of enhancing the productivity is the process for dividing the hydrogen generation into the microorganism culturing step and the hydrogen generating step.

To be particularly described below is the process for carrying out the hydrogen generation as divided into the microorganism culturing step and the hydrogen generating step. In the microorganism culturing step, firstly, the microorganism lacking in the hydrogen generating capability is cultured under aerobic conditions, and in the hydrogen generating step, then, the microorganism lacking in the hydrogen generating capability as obtained through proliferation in the preceding culturing step is allowed to induce the hydrogen generating capability under anaerobic conditions, followed by generation of hydrogen with use of such microorganism.

In the first place, there is to be described the step of culturing a microorganism under aerobic conditions. This step can permit the microorganism to be cultured to a high microorganism concentration in a short time. The means of culturing the microorganism can be practiced with use of the known means: the culturing means may be exemplified by culture under aerobic conditions, such as liquid culture, such as shaking culture, jar-fermenter culture and tank culture, etc. or solid culture, and the like. The culturing temperature can be appropriately varied within such a range as may allow the growth of a microorganism, and ordinarily ranges from about 15 to 40° C., and preferably from about 30 to 40° C. The pH value of the culture medium is preferably in the region of about 6 to 8. The culturing time varies depending upon the conditions of culture, and generally ranges preferably from about 0.5 to 5 days.

Then, there is to be described the step of inducing the hydrogen generating capability in a microorganism lacking in the hydrogen generating capability.

The procedure of inducing the hydrogen generating capability in a microorganism lacking in the hydrogen generating capability is preferably practiced under anaerobic conditions.

Culture under anaerobic conditions preferably includes stirring culture to promote the diffusion of ingredients in the culture medium. The microorganism concentration at the time of initiation of stirring culture under anaerobic conditions is preferably about 0.01 to 80% by mass (on the basis of the wet mass of microorganism). On the occasion of this, it is to be noticed that although the microorganism preferably divides and proliferates during stirring culture under anaerobic conditions so as to allow the microorganism to acquire the hydrogen generating capability, the microorganism is not necessarily required to divide and proliferate and may not divide and proliferate, only if the hydrogen generating capability may only be induced in the microorganism.

The meaning of "under anaerobic conditions" refers to the conditions in which the oxidation-reduction potential in the culture medium preferably ranges from about −100 to −500 mV, and more preferably from about −200 to −500 mV. As a procedure of adjusting the anaerobic conditions of the culture medium, any procedures may be preferably employable insofar as they remove dissolved oxygen in the culture medium, and include, for example, the procedure of removing dissolved gases by heat treatment or in-vacuo treatment of the culture medium or by bubbling with nitrogen gas, etc. through the culture medium, and the like. In particularly, the procedure of removing dissolved gases, especially dissolved oxygen, in the culture liquid, may be exemplified by a procedure of carrying out a degassing treatment under reduced pressure of preferably not more than about $13 \times 10^2$ Pa, more preferably not more than about $7 \times 10^2$ Pa, more preferably not more than about $4 \times 10^2$ Pa, for a period of preferably about 1 to 60 minutes, more preferably about 5 to 60 minutes, and the said procedures can permit the culture liquids under anaerobic conditions to be obtained. Alternatively, a reducing agent may be added to the culture liquid, as the case may be, to prepare the culture liquids under anaerobic conditions. The reducing agent to be used in the culture liquid includes, for example, thioglycolic acid, ascorbic acid, cysteine hydrochloride, mercaptoacetic acid, thiol acetic acid, glutathion or sodium sulfide, etc. These may be added singly or in combination of several kinds of agent to the culture liquid.

Culture for inducing the hydrogen generating capability in a microorganism under anaerobic conditions can be carried out in a conventionally used nutrient culture medium containing carbon sources, nitrogen sources, mineral sources and the like. The carbon source may be exemplified by glucose, fructose, galactose, mannose, xylose, arabinose, lactose, sucrose, cellulose, ribose, ribitol, arabinose, rhamnose, fucose, molasses or glycerol, etc. As the nitrogen source, there may be mentioned, for example, inorganic-form nitrogen source or organic-form nitrogen source. Examples of the inorganic-form nitrogen source include ammonia, ammonium salts or nitrates, etc. Examples of the organic-form nitrogen source include urea, amino acids, or proteins, etc. These inorganic-form nitrogen source and organic-form nitrogen source may be added singly or as a mixture to a nutrient culture medium. Both inorganic-form and organic-form sources may be used alike. As the mineral source, there may be used, for example, potassium monohydrogen phosphate or magnesium sulfate containing mainly K, P, Mg, S and the like. In addition, peptone, meat extract, yeast extract, corn steep liquor, casamino acid and nutrients, such as various vitamins inclusive of biotin or thiamine, etc. may be added to the culture medium as the case may be. The culture medium preferably contains trace metal components to generate hydrogen. Required trace metal components vary depending on the species of the microorganism to be cultured, and include, for example, iron, molybdenum, selenium or nickel, etc. These trace metal components are contained in natural nutrients, such as yeast extract and the like, in significant quantities.

The above-mentioned carbon source is required for the culture intended to induce the hydrogen generating capability under anaerobic conditions, and it is preferable to use a carbon source which is taken up by the microorganism at a slow rate. As such a carbon source, there may be mentioned, for example, lactose, galactose, arabinose, xylose, ribose, ribitol, arabitol, rhamnose or fucose, etc.

Referring to the microorganism concentrations, it is preferable to culture the microorganism at high microorganism concentrations under anaerobic conditions, because the hydrogen generating capability can be induced more effectively.

With reference to the conditions of stirring culture under anaerobic conditions, the temperature range desirably is about 20 to 45° C., and preferably about 25 to 40° C., while the pH range is preferably about 4.0 to 10.0, and more preferably about 5.0 to 8.0. Acids or alkalis can be used to adjust the pH range. Both the above-mentioned temperature and pH ranges are the optimum temperature and pH ranges for the using microorganism. Ordinarily, the carbon-source concentration at the initiation of culture is preferably about 0.1 to 20% (w/v) and more preferably 1 to 5% (w/v).

Then, there is to be described below the step of generating hydrogen with use of the microorganism having the hydrogen generating capability, as obtained by the above-described procedures.

After completion of the culture to induce the hydrogen generating capability, the microorganism having the hydrogen generating capability induced, as present in the culture medium, can be used as such or after being once separated by adding the separated microorganism under anaerobic conditions to a solution for the hydrogen generation maintained in the reductive condition. In both of these cases, an organic substrate can be supplied to the culture medium or the solution for the hydrogen generation to thereby enable the microorganism to generate hydrogen. Since the reaction of the hydrogen generation is carried out at a constant pH value to assure stable progress, it is preferable to add a component having a buffering action to the reaction solution. The buffer reagent usable in the hydrogen generation includes, for example, acid buffers reagent, such as phosphate buffer reagent, acetate buffer reagent, carbonate buffer reagent, etc., and Good's buffer reagents, such as MES, PIPES, ACES, HEPES, HEPPS, MOPS, TAPS or CAPS, etc., and the like. The concentration of buffer reagents and the type of reagents may be appropriately regulated and utilized depending upon the pH value of the reaction solution. It is preferable to maintain the pH value at ca. 5 to 8.

The procedure of generating hydrogen includes, for example, a procedure of supplying continuously or intermittently an organic substrate to a solution for the hydrogen generation containing the microorganism as added. Because the process for producing hydrogen according to the present invention makes effective use of the characteristic feature that any redundant, surplus components, such as lactic acid and succinic acid, etc., are not produced, preferred examples of an organic substrate to be supplied to the solution for the hydrogen generation include the organic substrates which are equivalent to the glycolysis intermediates being located upstream of phosphoenol pyruvic acid, and saccharides are more preferable from the standpoints of the easiness to be uptaken by the microorganism and the reduced costs.

In this context, the term "saccharides" generally refers to the substances consisting of $C_n(H_2O)_n$ as a chemical formula unit and includes monosaccharides, oligosaccharides, and polysaccharides. Their specific examples include glucose, maltose, meliobiose, galactose, lactose, trehalose, sucrose, cellobiose, fructose, mannose, sorbose, N-acetylglucosamine, D-glucosamine, fucose, rhamnose, arabinose, xylose, ribose, ribitol, arabitol, deoxyribose, glucitol, mannitol, galactitol, xylitol, glucuronic acid, galacturonic acid, gluconic acid, starch or glycogen, etc. From the viewpoint of efficient utilization by the microorganism, preferred among them is glucose, galactose, xylose, fructose or sucrose, and glucose and sucrose are more preferable.

The concentration of the organic substrate to be added to the solution for the hydrogen generation preferably ranges from ca. 1% (w/w) to the aqueous saturated solution, and more preferably from ca. 50% (w/w) to the aqueous saturated solution. Also, the organic substrate is desirably added in the solid state. Too much low concentrations of saccharides in the solution for the hydrogen generation is not preferable, because this brings about increases in volume of the solution for the hydrogen generation solution and changes in the microorganism concentration, as well, according as the supply of the organic substrate increases. Furthermore, the supply speed of the organic substrate is not particularly limited, insofar as the solution for the hydrogen generation is controlled at a pH value within the range of about 4 to 9.

The reaction temperature for the hydrogen generation is preferably in the range of about 20 to 50° C., and more preferably in the range of about 30 to 45° C. from the viewpoint of sustention of the microorganism's life.

As a solution for the hydrogen generation, it is required that a solution for the hydrogen generation is maintained under anaerobic conditions (reductive state). Referring to the anaerobic conditions of this solution, the solution for the hydrogen generation preferably shows an oxidation-reduction potential of ca. −100 to −500 mV, and more preferably ca. −200 to −500 mV.

The microorganism concentration in the solution for the hydrogen generation is preferably ca. 0.1 to 80% (w/w) (on the basis of wet mass of microorganism), and in view of an invariably increasing viscosity of the solution as higher microorganism concentration, it is more preferably about 0.1 to 70% (w/w) (on the basis of wet mass of microorganism).

Since the gas evolves vigorously, it is preferable to add a defoaming agent to the solution for the hydrogen generation. As a defoaming agent, use is made of the known ones, and particularly, there are preferably used silicone based ones (e.g., SI (Silicone), etc.) or polyether based ones (e.g., PE-H (Polyether-High), PE-M (Polyether-Medium), PE-L (Polyether-Low), etc.).

The microorganism, organic substrate and defoaming agent can be supplied to the solution for the hydrogen generation in accordance with the procedures known in the art.

To be described below is the fuel cell system using the process for producing hydrogen according to the present invention.

In the process for producing hydrogen according to the present invention, there is generated the gas composed mainly of hydrogen and carbon dioxide, without production of carbon monoxide. In utilizing hydrogen produced by the conventional methods, such as the reforming process of natural gas, as a fuel for Proton-Exchange-Membrane fuel cells, generally, it is necessary to use a system (CO transformer, CO eliminator etc.) for removing carbon monoxide from the gas containing hydrogen, etc. as obtained by the said process to thereby maintain the CO level at less than 10 ppm. Since the hydrogen gas produced by the process with use of the microorganism according to the present invention is entirely free of CO, it does not become necessary to set up the reforming unit for removing carbon monoxide within the fuel cell system, and consequently, the fuel cell system can be simplified. From the viewpoint of secured prolongation of lifetime of the fuel cell, additionally, it is preferable to use the gas produced by the process for producing hydrogen according to the present invention.

The conventional reforming process employed in the hydrogen generating apparatus with use of the city gas requires the reforming temperature of not less than 600° C., and even the reforming process using methanol necessitates the reforming temperature of several hundreds degrees Cels., whereas the reaction vessel to be used in the process for producing hydrogen according to the present invention may possibly be operated at nearly ambient temperature. Furthermore, the conventional reforming unit generally requires some length of time not only for the start-up but also for the shut-down. In contrast with this, however, the process for producing hydrogen according to the present invention, when used, facilitates the operation up to starting/stopping the production of hydrogen easy, and thus it is preferable to use the process for producing hydrogen according to the present invention in the fuel cell system.

In addition, the process for producing hydrogen according to the present invention is superior to the process for producing hydrogen on the basis of the chemically reforming process of fossil fuels in terms of the facts that the fuel cell system using the process for producing hydrogen according to the present invention does not produce CO, resulting in reduced concerns over the deterioration of the fuel cell; the process as a method for supplying hydrogen eliminates the need to set up the reforming unit system to be run at high temperatures; and hydrogen can be produced simultaneously with supply of the organic substrate, and the like.

EXAMPLES

The present invention is to be described below in more detail by way of examples, but the present invention is not understood to be limited thereto.

Example 1

Construction of the ldhA-Inactivated Strain of *Escherichia coli* (w3110 Strain:ATCC 27325) (Hereinafter Referred to as "ldhA-Inactivated Strain") and a frdBC-Inactivated Strain of Said *Esherichia coli* (Hereinafter Referred to as "frdBC-Inactivated Strain"):

(1) Extraction of the Genome DNA

The said strain of *Escherichia coli* was cultured under shaking in 10 mL of the LB culture medium (Luria-Bertani culture medium) shown in Table 1 at 37° C. overnight, and the genome DNA was extracted using GenomicPrep Cells and Tissue DNA Isolation Kit (produced by Amersham Bioscience).

TABLE 1

| Composition of the LB culture medium | |
|---|---|
| Composition ingredients | Ingredient amount |
| Water | 1000 ml |
| Tryptone | 10 g |
| Yeast extract | 5 g |
| Sodium chloride | 5 g |

(2) Preparation of the Vector for Construction of the Strain Having ldhA Inactivated (Disrupted)

From the genome DNA obtained above under (1), the ldhA region was amplified with use of a thermal cycler, GeneAmp PCR System 9700 (produced by ABI), and using the primers:

```
5'-CCTGTTTCGCTTCACCGGTCAG-3'    (SEQ ID NO: 1)

5'-TCTTTGGTTCTGTCCAGTACCG-3'    (SEQ ID NO: 2)
```

The amplified DNA and plasmid pHSG398 (produced by TAKARA SHUZO CO., LTD.) were digested with BamHI and PstI, followed by ligation with use of DNA Ligation Kit ver. 2.1 (produced by TAKARA SHUZO CO., LTD.) to give ldhA-pHSG398. Inverse PCR was conducted with the obtained ldhA-pHSG398 as a template and the primers:

```
                                 (SEQ ID NO: 3)
5'-GGACTAGTCTGGCGTTCGATCCGTATCC-3'

(SEQ ID NO: 4)
5'-GCTCTAGACCAAAACCTTTCAGAATGCGCA-3',
``` followed by digestion with SpeI and XbaI. Inserted into the resultant DNA was the chloramphenicol cassette that was amplified from pHSG398 as a template using the primers:

```
5'-GCTCTAGAACGGAAGATCACTTCGCAGAAT-3' (SEQ ID NO: 5)

5'-GGACTAGTTTAAGGGCACCAATAACTGCCT-3' (SEQ ID NO: 6)
``` and the vector ΔldhA-pHSG398 was obtained.

Also, the sacB region amplified by PCR from pMV5 (Vertes, A. A., et al., Isolation and characterization of IS31831, a transposable element from *Corynebacterium glutamicum*. Mol. Microbiol., 11, 739-746 (1994)) using the primers:

```
5'-CTCTGCATGCAACCCATCACATATACCTGC-3'  (SEQ ID NO: 7)

5'-CTCTGCATGCATCGATCCTCTAGAGTATCG-3'  (SEQ ID NO: 8)
``` and the plasmid pTH18ks1 (Hashimoto-Gotoh, T. et al., A set of temperature sensitive-replication/-segregation and temperature resistant plasmid vectors with different copy numbers and in an isogenic background (chloramphenicol, kanamycin, lacZ, repA, par, polA). Gene 241, 185-191 (2000)) were digested with SphI, followed by ligation to give sacB-pTH18ks1.

Then the ΔldhA region of ΔldhA-pHSG398 was inserted between the BamHI and PstI sites of the resultant sacB-pTH18ks1 to give ΔldhA-sacB-pTH18ks1. FIG. 1 shows the construction of ΔldhA-sacB-pTH18ks1.

(3) Transfection of ΔldhA-sacB-pTH18ks1 and Construction of the ldhA-Inactivated Strain.

The ΔldhA-sacB-pTH18ks1 obtained by the above-described procedure was electroporated into the W3110 strain. Then homologous recombination was carried out by cultivation in a culture medium (10 mL) shown in Table 2 below at 43° C. to thereby give the recombinant strain having the recombinant vector inserted into chromosomes.

TABLE 2

Composition of the culture medium (LB culture medium containing chloramphenicol)

| Composition ingredients | Ingredient amount |
| --- | --- |
| Water | 1000 ml |
| Tryptone | 10 g |
| Yeast extract | 5 g |
| Sodium chloride | 5 g |
| Chloramphenicol | 50 mg |

The recombinant strain obtained in the above agar culture medium was cultivated in the agar culture medium (10 mL) shown in Table 3 at 30° C. to give the ldhA-inactivated strain.

TABLE 3

Composition of the culture medium (sucrose containing minimum medium)

| Composition ingredient | Ingredient amount |
| --- | --- |
| Water | 1000 ml |
| Potassium dihydrogen phosphate | 2 g |
| Dipotassium hydrogen phosphate | 7 g |
| Ammonium sulfate | 1 g |
| Magnesium sulfate heptahydrate | 0.1 g |
| Thiamine hydrochloride | 20 mg |
| Sucrose | 100 g |
| Agar | 15 g |

(4) Molecular Biological Identification of the ldhA-Inactivated Strain

The ldhA-inactivated strain as obtained by the above-described procedure was identified by the sequencer Prism 3100 genetic analyzer (supplied by ABI) as the strain having the ldhA region of W3110 strain disrupted.

(5) Preparation of the Vector for Inactivating frdBC

Form the genome DNA obtained in the above (1), the frdABCD region was amplified by use of a thermal cycler, GeneAmp PCR System 9700 (available from ABI), and using primers:

```
                                 (SEQ ID NO: 9)
5'-GCGAGCTCGTGCAAACCTTTCAAGCCGA-3'

(SEQ ID NO: 10)
5'-CGGGATCCGACACCAATCAGCGTGACAA-3'.
```

The amplified DNA and plasmid pHSG398 (available from TAKARA SHUZO CO., LTD.) were digested with BamHI and SacI, followed by ligation with use of DNA ligation Kit ver 2.1 (produced by TAKARA SHUZO CO., LTD.) to give frd ABCD-pHSG398.

Then, inverse PCR was conducted with the resultant frd ABCD-pHSG398 as a template using the primers:

```
                                 (SEQ ID NO: 11)
5'-CCGCTCGAGCTGAACCCAGAGTTCATCGG-3'

(SEQ ID NO: 12)
5'-CCGCTCGAGAACGTACGCTTTCGCCAGTT-3'
``` followed by digestion with XhoI. Inserted into the resultant DNA was the kanamycin cassette that was amplified from pUC4K (produced by Amersham Bioscience) as a template using the primers:

(SEQ ID NO: 13)
5'-CCGCTCGAGGAAGATGCGTGATCTGATCCT-3'

(SEQ ID NO: 14)
5'-CCGCTCGAGGCCACGTTGTGTCTCAAAATC-3' and there was obtained the vector ΔfrdBC-pHSG398.

Figure 2:
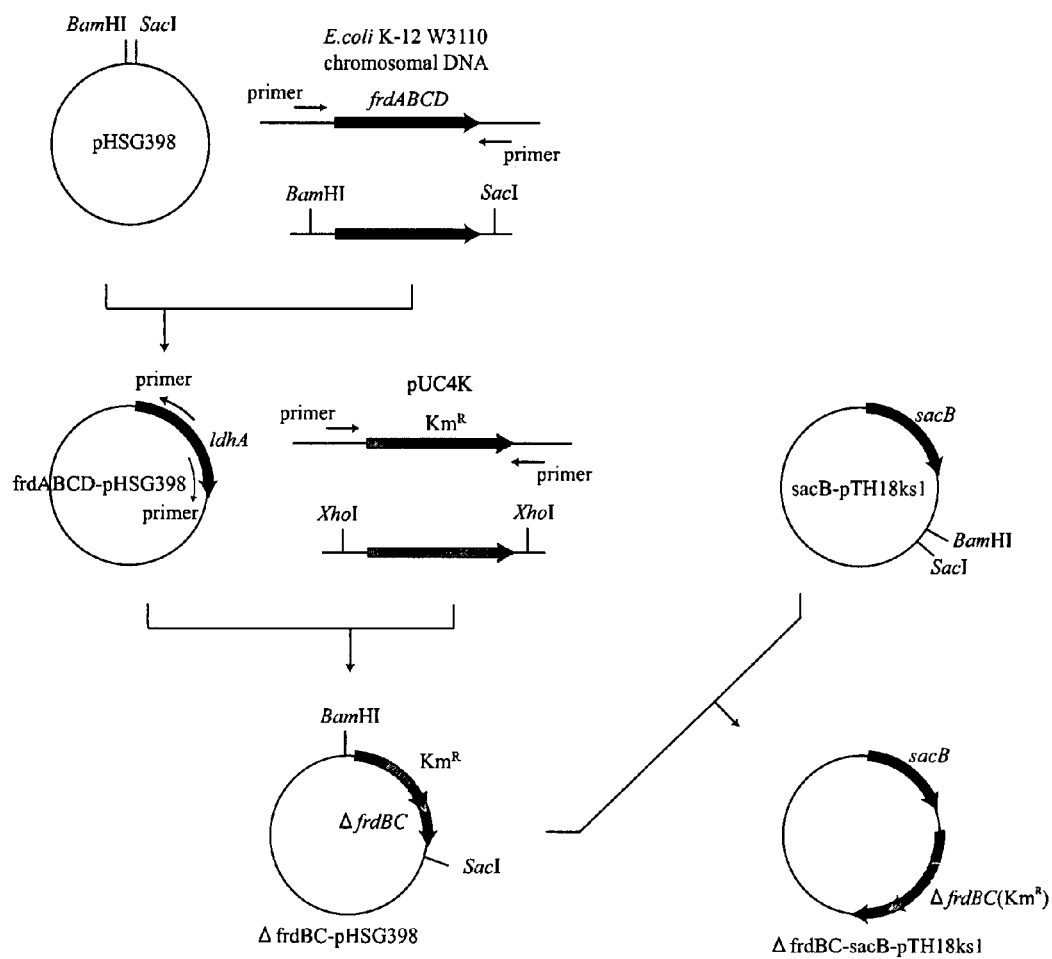
FIG. 2 is a schematic view showing the construction of ΔfrdBC-sacB-pTH18ks1.

Then, the ΔfrdBC region of ΔfrdBC-pHSG398 was inserted between the BamHI and SacI sites of the resultant sacB-pTH18ks1 to give ΔfrdBC-sacB-pTH18ks1. FIG. 2 shows the construction of ΔfrdBC-sacB-pTH18ks1.

(6) Transfection of ΔfrdBC-sacB-pTH18ks1 and Preparation of the frdBC-Inactivated Strain.

ΔfrdBC-sacB-pTH18ks1 obtained by the procedure described above under (5) was electroporated into the ldhA-inactivated strain as obtained under (3). Then, homologous recombination was performed by culture in a culture medium (10 mL) shown below in Table 4 at 43° C. to give a recombinant strain having the recombinant vector inserted into chromosomes.

The above-obtained recombinant strain was cultured in the agar culture medium (10 mL) shown in Table 3 at 30° C. to give the ldhA- and frdBC-inactivated strain of Escherichia coli (hereinafter referred to as "ldhA- and frdBC-inactivated strain").

TABLE 4

Composition of the culture medium (kanamycin containing LB medium)

| Composition ingredients | Ingredient amount |
|---|---|
| Water | 1000 ml |
| Tryptone | 10 g |
| Yeast extract | 5 g |
| Sodium chloride | 5 g |
| Kanamycin | 50 mg |

(7) Molecular Biological Identification of frdBC-Inactivated Strain

The ldhA- and frdBC-inactivated strain as obtained by the above-described procedure was identified by a sequencer, Prism 3100 geneticanalyzer (available from ABI), as the strain having the ldhA and frdBC regions of the said strain of Escherichia coli disrupted.

The W3110 strain transformed by the above-described procedure in this Example was named W3110 ΔldhA ΔfrdBC, and deposited, on Dec. 20, 2005, with Patent Organism Depositary Center, National Institute of Advanced Industrial Science and Technology of Japan (located at Tsukuba Central 6, 1-1-1 Higashi, Tsukuba, Ibaraki, Japan) under the accession No. FERM P-20737, and also deposited, on Nov. 13, 2006, with the same organization, International Depository Authority, under the accession No. FERM BP-10726.

Example 2

The Process for Producing Hydrogen from Glucose with Use of the ldhA- and frdBC-Inactivated Strain as Obtained in Example 1

(1) Cultivation Under Aerobic and Anaerobic Conditions

The ldhA- and frdBC-inactivated strain as obtained in Example 1 was added to 10 mL of the culture medium having the composition shown in Table 5 and cultured under shaking overnight at 37° C. under aerobic conditions.

10 mL of the culture medium containing the ldhA- and frdBC-inactivated strain as cultured under shaking overnight was inoculated onto 1.0 L of the culture medium shown in Table 5, followed by culture under anaerobic conditions. Cultivation under anaerobic conditions was performed in the anaerobic chamber system (manufactured by Coy Co.) having an atmosphere of 95% nitrogen and 5% hydrogen. The culture under anaerobic conditions was conducted for 12 hours at 37° C., while maintaining the culture medium at pH 6.0 (adjusted with 5N NaOH). The resultant culture medium was subjected to a centrifuge (at 6500 rpm, 20 minutes), followed by removal of the supernatant to give about 4 g (wet weight) of microbial cells.

TABLE 5

Composition of the culture medium

| Composition ingredients | Ingredient amount |
|---|---|
| Water | 1000 ml |
| Glucose | 30 g |
| Diammonium hydrogen phosphate | 10 g |
| Potassium sulfate | 2 g |
| Sodium chloride | 0.3 g |
| Magnesium sulfate | 0.2 g |
| Iron sulfate | 4 mg |
| Zinc sulfate | 0.9 mg |
| Copper sulfate | 0.4 mg |
| Manganese sulfate | 0.2 mg |
| Calcium chloride | 0.8 mg |
| Sodium tetraborate | 0.09 mg |
| Ammonium (6-) heptamolybdate | 0.4 mg |
| Ammonium nickel sulfate | 0.9 mg |
| Sodium selenite | 0.6 mg |
| Kanamycin | 50 mg |

(2) Hydrogen Generation Reaction

The resultant microbial cells were suspended in 100 mL of a solution for the hydrogen generation having the composition shown below in Table 6 in such a manner that the cell density might be 4% (on the basis of microbial cell mass in the wet state).

TABLE 6

Composition of the solution for the hydrogen generation

| Composition ingredients | Ingredient amount |
|---|---|
| Water | 1000 ml |
| Yeast extract | 0.5% (wt. %) |
| Tryptone peptone | 1.0% (wt. %) |
| Sodium molybdate | 10 μM |
| Sodium selenite | 10 μM |
| Disodium hydrogen-phosphate | 26.5 mM |
| Sodium dihydrogen-phosphate | 73.5 mM |
| Defoaming agent | 0.01% (wt. %) |

The thus-prepared microbial cell suspension for the hydrogen generation was admixed with a 3M aqueous solution of glucose under anaerobic conditions (95% nitrogen and 5% hydrogen), and the hydrogen generating capability of the microorganism was evaluated, wherein the glucose concentration in the microbial cell suspension for the hydrogen generation was adjusted to 60 mM.

The hydrogen generating capability of the microbial cells was measured by the procedure of collecting hydrogen through water. The gas evolved immediately after addition of glucose, and the initial rate of hydrogen generation was determined from the volume of the gas generated in 10 minutes after addition of glucose.

Analysis by gas chromatography (manufactured by Shimadzu Corporation) of the generated gas as collected revealed that the generated gas contains ca. 60% by volume of hydrogen and ca. 40% by volume of a gas (carbon dioxide gas). The hydrogen yield and rate of hydrogen generation as calculated are presented below in Table 7.

Example 3

The Process for Producing Hydrogen from Fructose with Use of the ldhA- and frdBC-Inactivated Strain as Obtained in Example 1

The initial rate of hydrogen generation and hydrogen yield were measured by the same procedure as described in Example 2 except that a 3M aqueous solution of fructose was used instead of a 3M aqueous solution of glucose for the reaction of hydrogen generation. The hydrogen yield and rate of hydrogen generation as found are shown below in Table 8.

Comparative Example 1 and Comparative Example 2

Method for Culturing the Microbial Cells for the Hydrogen Generation with Use of the W3110 Strain (ATCC 27325) of *Escherichia coli* Having the ldhA and frdBC Genes not Inactivated, and Reaction for the Hydrogen Generation Cultivation under aerobic conditions as well as cultivation under anaerobic conditions were conducted by the same procedures as described in Examples 2 and 3, except that the W3110 strain (ATCC 27325), a wild-type strain of *Escherichia coli*, was used in place of the ldhA- and frdBC-inactivated strain, to thereby measure the hydrogen yield and initial rate of hydrogen generation. The cases where glucose and fructose were used individually as a substrate were made Comparative Examples 1 and 2, respectively.

Comparative Example 3 and Comparative Example 4

Method for Culturing the Microbial Cells for the Hydrogen Generation with Use of the W3110 ΔldhA Strain of *Escherichia coil* Having the ldhA Gene Alone Inactivated and Reaction for the Hydrogen Generation Cultivation under aerobic conditions as well as cultivation under anaerobic conditions were conducted by the same procedures as described in Examples 2 and 3, except that the W3110 ΔldhA strain of *Escherichia coil* having the ldhA gene inactivated was used in place of the ldhA- and frdBC-inactivated strain, to thereby measure the hydrogen yield and initial rate of hydrogen generation. The cases where glucose and fructose were used individually as a substrate were made Comparative examples 3 and 4, respectively.

Table 7 shows the results of measuring the hydrogen yield and rate of hydrogen generation in Example 2 and Comparative Examples 1 and 3. Table 8 shows the results of measuring the hydrogen yield and rate of hydrogen generation in Example 3 and Comparative Examples 2 and 4.

It is definite and obvious from Tables 7 and 8 that the hydrogen yield and rate of hydrogen generation were significantly improved when the ldhA- and frdBC-inactivated strain was used for the hydrogen generation (Examples 2 and 3), as compared with the control strains (Comparative Examples 1 to 4).

TABLE 7

Hydrogen generation from glucose

| | Example 2 W3110 ΔldhA ΔfrdBC | Comparative Example 1 W3110 | Comparative Example 3 W3110 ΔldhA |
|---|---|---|---|
| Hydrogen yield from 1 mol of glucose (mol/mol glucose) | 1.82 | 1.08 | 1.11 |
| Rate of hydrogen generation from glucose (mmol/h/g dry microbial cells) | 13.4 | 9.5 | 9.8 |

TABLE 8

Hydrogen generation from fructose

| | Example 3 W3110 ΔldhA ΔfrdBC | Comparative Example 2 W3110 | Comparative Example 4 W3110 ΔldhA |
|---|---|---|---|
| Hydrogen yield from 1 mol of fructose (mol/mol glucose) | 1.80 | 1.05 | 1.10 |
| Rate of hydrogen generation from fructose (mmol/h/g dry microbial cells) | 13.1 | 9.2 | 9.5 |

What is claimed is:

1. A process for producing hydrogen comprising culturing a transformant of *Escherichia coli* K-12 W3110 strain under aerobic conditions then culturing said transformant under anaerobic conditions to induce the hydrogen generating capability, and further culturing the transformant having the hydrogen generating capability under anaerobic conditions in the presence of a saccharide to produce hydrogen, wherein the transformant of *Escherichia coli* K-12 W3110 strain is the W3110 ΔldhA ΔfrdBC strain of *Escherichia coli* deposited with International Patent Organism Depositary Authority, National Institute of Advanced Industrial Science and Technology of Japan under the accession No. FERM P-20737 and the international accession No. FERM BP-10726.

2. The process for producing hydrogen according to claim 1, wherein the saccharide is selected from the group consisting of glucose, galactose, xylose, sucrose and fructose.

3. The process of claim 1, wherein the transformant is cultured in a solution under anaerobic conditions, said solution having an oxidation-reduction potential of about −200 to −500 mV.

4. The process of claim 1, wherein the saccharide is supplied continuously or intermittently in an amount of about 50% (w/w) as an aqueous saturated solution or as a solid.

5. The process of claim 1, wherein the transformant is cultured in the presence of a defoaming agent.

* * * * *